United States Patent
Gruning et al.

(10) Patent No.: US 6,313,260 B2
(45) Date of Patent: *Nov. 6, 2001

(54) COPOLYMERIC, HYDROPHOBICALLY MODIFIED POLYASPARTIC ESTERS HAVING INCREASED MOLECULAR MASS AND THEIR USE

(75) Inventors: Burghard Gruning; Jorg Simpelkamp; Christian Weitemeyer, all of Essen (DE)

(73) Assignee: Goldschmidt AG, Essen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/312,222

(22) Filed: May 14, 1999

(30) Foreign Application Priority Data

May 20, 1998 (DE) ............................................. 198 22 600

(51) Int. Cl.$^7$ .................................................. C08G 69/08
(52) U.S. Cl. ......................... 528/310; 528/328; 528/363; 525/419; 525/420
(58) Field of Search .................................... 528/310, 328, 528/363; 525/419, 420

(56) References Cited

U.S. PATENT DOCUMENTS 5,219,952   6/1993   Koskan et al. .
5,910,564 * 6/1999   Gruning et al. ..................... 528/310

FOREIGN PATENT DOCUMENTS

| | | |
|---|---|---|
| 36 26 672 A1 | 2/1988 | (DE) . |
| 43 00 020 A1 | 7/1994 | (DE) . |
| 44 20 642 A1 | 12/1995 | (DE) . |
| 195 45 678 A1 | 6/1997 | (DE) . |
| 0 578 449 A1 | 1/1994 | (EP) . |
| 0 612 784 A1 | 8/1994 | (EP) . |
| 0 659 875 A2 | 6/1995 | (EP) . |
| WO92/14753 | 9/1992 | (WO) . |
| WO 95/35337 | 12/1995 | (WO) . |
| WO 96/08523 | 3/1996 | (WO) . |

OTHER PUBLICATIONS

Kovaks, et al., "Synthesis and Inhibitory Activity of Polyaspartic Acid Derivatives," J. Med. Chem., vol. 10, pp. 904–907 (1967).

Neri, et al., "Synthesis of α, β–Poly [(2–hydorxyethyl)–D-L–Aspartamide], a New Plasma Expander", J. Med. Chem., vol. 16, No. 8, pp. 893–897, (1973).

Neuse, et al., "Water–Soluble Polyamides as Potential Drug Carriers," Applied Macromolecular Chemistry and Physics, vol. 192, pp. 35–50, (1991).

H. Tamatani, et al., Superabsorbent Polymers Synthesized From Amino Acids, Annu. Tech. Conf. Soc. Plast. Eng. 1995, 53, 1510–13.

* cited by examiner

*Primary Examiner*—Duc Truong
(74) *Attorney, Agent, or Firm*—Scully, Scott, Murphy & Presser

(57) ABSTRACT

A high molecular weight copolymeric polyaspartic ester which has been hydrophobically modified with alkyl or alkenyl radicals having from 6 to 30 carbon atoms. The copolymers are derived from polyamino acids and have a molecular weight, $M_w$, of about 2500 or above.

10 Claims, No Drawings

COPOLYMERIC, HYDROPHOBICALLY MODIFIED POLYASPARTIC ESTERS HAVING INCREASED MOLECULAR MASS AND THEIR USE

BACKGROUND OF THE INVENTION

1. Field of the Invention

The present invention describes the preparation of high molecular weight copolymeric polyaspartic esters which have been hydrophobically modified with alkyl or alkenyl radicals having from 6 to 30 carbon atoms.

2. Prior Art

Polyamino acid derivatives, in particular polyaspartic acid, have recently attracted particular attention because of their biodegradability and their similarity to naturally occuring structures. Proposed applications are inter alia as biodegradable complexing agents, water softeners and detergent builders. Polyaspartic acid is generally obtained by alkaline hydrolysis of the direct synthesis precursor polysuccinimide (PSI, anhydropolyaspartic acid), the cyclic imide of polyaspartic acid. PSI can be prepared, for example, in accordance with EP 0 578 449 A, WO 92/14753, EP 0 659 875 A or DE 44 20 642 A from aspartic acid, or is obtainable, for example according to DE 36 26 672 A, EP 0 612 784 A, DE 43 00 020 A or U.S. Pat. No. 5,219,952 A, from maleic acid derivatives and ammonia. Proposed applications for these customary polyaspartic acids are inter alia as an encrustation inhibitor, builders in detergents, fertilizer additive and auxiliary in tanning.

The reaction of polysuccinimide with amines, which has been described by various working groups, leads to polraspartic amides (Kovacs et al., J. Med. Chem. 1967, 10, 904–7; Neuse, Angew. Makromol. Chem. 1991, 192, 35–50). The ring opening of polysuccinimide using polyamines and the subsequent alkaline hydrolysis for the preparation of polyaspartic acid derivatives for applications as superabsorbers is described, for example, in WO 95/35337, in WO 96/08523 or in Annu. Tech. Conf. Soc. Plast. Eng. 1995, 53, 1510–13. Neri et al describe, in J. Med. Chem 1973, 16, 893–897 the reaction of polysuccinimide with ethanolamine to give hydroxyethyl polyaspartates for pharmaceutical uses.

For applications inter alia as emulsifier, dispersant and surfactant, copolymeric polyaspartic esters partially esterified with long-chain fatty alcohols or their derivatives are of particular interest. Such compounds are readily obtainable on the basis of maleic monoesters and ammonia, as explained in DE 195 45 678 or EP 96 118 806.7, and generally more usually have low molecular weights.

The object of the invention is to provide copolymeric polyaspartic esters with increased molecular masses.

SUMMARY OF THE INVENTION

The object is achieved according to the invention by copolymeric polyaspartic esters having increased molecular mass, which are prepared from maleic acid derivatives and ammonia with the addition of di- or polyfunctional alcohols or amines.

DETAILED DESCRIPTION OF THE INVENTION

The copolymers used, which are derived from polyaspartic acid, consist, in an amount up to at least 75 mol % of the units present, of structural units of the general formulae (I), (II) and (III)

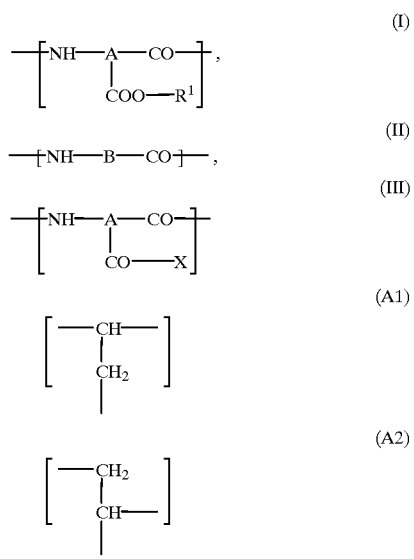

in which the structural elements A are identical or different trifunctional hydrocarbon radicals having 2 carbon atoms of the type (A1) or (A2), where one copolymer consists of at least three units of the formula (I), where $R^1$ is as defined for $R^2$, $R^3$ or $R^4$, where $R^2$ are one or more radicals from the group of alkali metals, alkaline earth metals, hydrogen or ammonium, $[NR^5R^6R^7R^8]^+$, where $R^5$ to $R^8$ independently of one another are hydrogen, alkyl or alkenyl having from 1 to 22 carbon atoms or hydroxyalkyl having from 1 to 22 carbon atoms and from 1 to 6 hydroxyl groups and/or their acylation products containing $C_1$- to $C_{22}$-carboxylic acid radicals, $R^3$ are identical or different, straight-chain or branched, saturated or unsaturated alkyl or alkenyl radicals $R^9$ having from 6 to 30 carbon atoms or radicals of the structure $-Y-R^9$, where Y is an oligo- or polyoxyalkylene chain having from 1 to 100 oxyalkylene units, $R^4$ are identical or different, straight-chain or branched, saturated or unsaturated alkyl or alkenyl radicals having from 1 to 5 carbon atoms, the units of the formula (II) are proteinogenic or nonproteinogenic amino acids and are present in an amount of not more than 20% by weight, based on the copolymeric polyaspartic acid derivatives and X in the formula (III) is one or more di- or polyfunctional radicals derived from molecular-mass-increasing agents, in particular a di- or polyhydroxy compound, a di- or polyamino compound, or aminoalcohols, having a linear, branched or cyclic, saturated, unsaturated or aromatic hydrocarbon structure, optionally oxo- or aza-substituted with O or N atoms in the chain, and at least in each case one radical $R^1$ must assume the meaning of $R^2$ and at least one radical $R^1$ that of $R^3$ and at least one radical $R^1$ that of X.

All of the data given relating to the composition of the polymeric products refer, as usual, to the average composition of the polymer chain.

The remaining units, which do not have the structure (I) or (II) or (III) (no more than 25 mol % of all units), can inter alia be iminodisuccinate units of the general formula (IV)

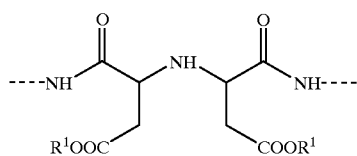

(IV)

and various end groups, on the N-terminus, for example aspartic acid, maleic acid, fumaric acid and malic acid units and their esters or amides, maleimide units or diketopiperazines derived from aspartic acid and/or the amino acid units (II), and esters or amides of the units (II), on the C-terminus, for example aspartic acid or malic acid units, their mono- or diesters, amides or cyclic imides.

Suitable amino acid units (II) from the group of proteinogenic amino acids are, for example, glutamine, asparagine, lysine, alanine, glycine, tyrosine, tryptophan, serine and cysteine and their derivatives; nonproteinogenic amino acids can, for example, be β-alanine, ω-amino-1-alkanoic acids, for example 6-aminocaproic acid, etc.

Surprisingly, these derivatives exhibit clear advantages, in terms of their application properties, over the analogous compounds having a relatively low molecular weight, in particular as regards the thermal and long-term stability of the preparations in the field of cosmetic W/O and O/W emulsions and for pigment dispersions for coatings and colorants.

According to the invention, preference is given to compounds in which at least one free carboxylate group ($R^1$=H, metal, ammonium) is present, at least one radical $R^3$ includes identical or different radicals of the structure $R^9$-Y-, where $R^9$ originates from the group of straight-chain or branched, saturated or unsaturated alkyl or alkenyl radicals having from 6 to 30 carbon atoms (for example branched or linear octyl, decyl, dodecyl, tetradecyl, hexadecyl, octadecyl or docosyl radicals, also unsaturated and polyunsaturated species such as, for example, oleyl) and Y is a polyoxyalkylene chain having from 0 to 100 alkylene glycol units, preferably derived from ethylene oxide, propylene oxide or mixtures thereof, and optionally a radical $R^4$ originates from the group of straight-chain or branched, saturated or unsaturated alkyl or alkenyl radicals having from 1 to 5 carbon atoms (for example methyl, ethyl, n-propyl, i-propyl, n-butyl, i-butyl, s-butyl, n-pentyl) and at least one polyfunctional radical X, preferably derived from a saturated di- or polyhydroxy or a di- or polyamino compound, such as, for example, linear 1, (-alkanediols, glycerol, sorbitol, 1,2-propylene glycol, linear 1, (-diaminoalkanes, lysine, ethanolamine, diethanolamine, triethanolamine, sugar derivatives, oligo- and polysaccharides, and the addition products of said compounds with ethylene oxide and/or propylene oxide. Other suitable polyfunctional compounds are, for example, polyvinyl alcohol, oligo- and polyethylene glycols or ethylene oxide-propylene oxide copolymers.

A preferred form of the copolymers comprises alkyl or alkenyl radicals $R^9$ having from 10 to 22 carbon atoms without alkylene glycol spacers (alkylene glycol chain length 0), crosslinking groups (III) derived from 1, (-diols and diamines having from 4 to 6 carbon atoms, polyethylene glycols having a molecular mass of from 200 to 2000 or mono-, di- or triethanolamine, and optionally small amounts of alkyl or alkenyl radicals $R^4$ having from 1 to 4 carbon atoms.

These derivatives are obtainable, for example, by a preparation process which comprises reacting a mixture of monoesters of monoethylenically unsaturated dicarboxylic acids with from 0.1 to 3.0 equivalents of ammonia, preferably with from 0.8 to 1.5 equivalents of ammonia, or thermally converting the ammonium salts of these acids into the polymer. Use can be made, for example, of derivatives of maleic acid, fumaric acid, itaconic acid, alkenylsuccinic acid, alkylmaleic acid, citraconic acid or their ammonium salts, preferably derivatives of maleic acid, fumaric acid or itaconic acid, particularly preferably maleic acid derivatives of the general formulae (V) und (VI)

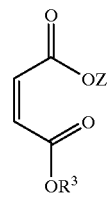

(V)

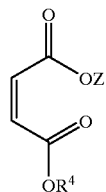

(VI)

where Z is hydrogen or ammonium, and $R^3$ and $R^4$ are the above defined radicals. These maleic acid derivatives can in each case be used alone or in any desired mixtures with one another.

Preferred radicals $R^3$ are alkyl radicals having from 8 to 30 carbon atoms, for example linear or branched decyl, dodecyl, tetradecyl, hexadecyl or octadecyl radicals and unsaturated alkenyl radicals, such as, for example, oleyl. Preferred radicals $R^4$ are alkyl radicals having from 1 to 4 carbon atoms, preferably methyl, ethyl, n-propyl, i-propyl, n-butyl, i-butyl or s-butyl.

The reaction can be carried out with or without the addition of organic solvents. Examples of suitable solvents are alcohols, ketones, esters, oligo- and poly(alkylene) glycols and glycol ethers, dimethyl sulfoxide, dimethylformamide, N,N-dimethylacetamide or N-methylpyrrolidone and their mixtures, etc. Preference is given to using alcohols having from 2 to 4 carbon atoms, particularly preferably the short-chain alcohol $R^4OH$, and ketones such as, for example, methyl isobutyl ketone or methyl isoamyl ketone, or alkyl esters of carboxylic acids having from 1 to 4 carbon atoms, such as, for example, sec-butyl acetate or pentyl acetate. The reaction can optionally be carried out in the presence of compatibility-promoting agents. These may be surface-active compounds, for example addition products of from 1 to 30 mol of ethylene oxide and/or from 0 to 5 mol of propylene oxide with $C_{12}$–$C_{30}$-fatty alcohols and wool wax alcohols; ethylene oxide addition products of glycerol mono- and diesters and sorbitan mono- and diesters of saturated and unsaturated fatty acids having from 6 to 22 carbon atoms; addition products of from 2 to 30 mol of ethylene oxide and/or from 0 to 5 mol of propylene oxide with fatty acids having from 12 to 22 carbon atoms and with alkylphenols having from 8 to 15 carbon atoms in the alkyl group; $C_{12}$–$C_{18}$-fatty acid partial esters of addition products of from 1 to 30 mol of ethylene oxide with glycerol; addition products of ethylene oxide with fats and oils, for example castor oil or hydrogenated castor oil; partial esters of saturated or unsaturated $C_{12}$–$C_{22}$-fatty acids, including branched or hydroxyl-substituted ones, with polyols, for example esters of glycerol, ethylene glycol, polyalkylene glycols, pentaerythritol, polyglycerol, sugar alcohols such as sorbitol, and polyglucosides such as cellulose; polysiloxane-polyalkyl-polyether copolymers and their derivatives and hydrophobically modified polyaspartic acid derivatives, for example partially esterified polyaspartic acids, partially esterified polyaspartic acid-co-glutamic acid or condensates of maleic monoesters and ammonia, prepared, for example, by the novel process or as in DE 195 45 678 A, the preparation process of said polyamino acid derivatives having no influence on their compatibility-promoting effect. If desired, a certain fraction of the product mixture may also remain in the reactor and be used as solubilizer for a subsequent reaction.

The compatibility- or solubility-promoting agents present may also be cationic surfactants, for example from the group of quaternary ammonium compounds, quaternized protein hydrolysates, alkylamido amines, quaternary ester compounds, quaternary silicone oils or quaternary sugar and polysaccharide derivatives, anionic surfactants, for example from the group of sulfates, sulfonates, carboxylates and mixtures thereof, for example alkylbenzenesulfonates, α-olefinsulfonates, α-sulfonated fatty acid esters, fatty acid glycerol ester sulfates, paraffinsulfonates, alkyl sulfates, alkyl polyether sulfates, alkyl sulfosuccinates, fatty acid salts (soaps), fatty acid esters of polylactic acid, N-acylamino acid esters, N-acyltaurates, acylisethionates, ether carboxylates, monoalkyl phosphates, N-acylamino acid derivatives, such as N-acyl aspartates or N-acyl glutamates, N-acylsarcosinates, amphoteric or zwitterionic surfactants, such as, for example, alkylbetaines, alkylamidoalkylbetaines of the cocoamidopropylbetaine type, sulfobetaines, phosphobetaines, sultaines and amidosultaines, imidazolinium derivatives, amphoglycinates, or nonionic surfactants, such as, for example, oxethylated fatty alcohols, oxethylated alkylphenols, oxethylated fatty acid esters, oxethylated mono-, di- or triglycerides or polyalkylene glycol fatty acid esters, sugar esters, for example fatty acid esters of sucrose, fructose or of methyl glucoside, sorbitol fatty acid esters and sorbitan fatty acid esters (optionally oxethylated), alkyl or alkenyl polyglucosides and their ethoxylates, fatty acid N-alkylpolyhydroxyalkylamides, polyglycerol esters, fatty acid alkanolamides, long-chain tertiary amine oxides or phosphine oxides and dialkyl sulfoxides.

The compatibility-promoting agents preferably remain in the product. In a preferred procedure, the reaction to give the copolymer is carried out with aqueous or gaseous ammonia at temperatures of from 0 to 150° C., preferably from 50 to 140° C., and subsequent distillation is carried out at from 70 to 240° C., preferably from 110 to 150° C., under reduced pressure, for example in kneading devices, high-viscosity reactors, extruders or stirred reactors, optionally using high-shear-force stirrers such as Mig or Intermig stirrers.

Under the reaction conditions, some of the ester groups, preferably those derived from $R^4OH$, are at the same time hydrolyzed and the desired carboxylic acid or carboxylate groups liberated. Subsequent mild partial or complete hydrolysis, preferably of the ester functions derived from the short-chain alcohol $R^4OH$, can, if desired, increase further the amount of free acid groups, for example by reaction with water, optionally in the presence of acids or bases, or with alkali metal hydroxides, optionally in the presence of an organic solvent or cosolvent.

By adding amino- and carboxy-functional compounds to the reaction mixture, it is possible to obtain copolymers in which the offered units are bonded via amide bonds. Suitable units are amino acids from the group of 20 proteinogenic amino acids which are present as monomers in all natural proteins, in an enantiomerically pure or racemic form, such as, for example, glutamine, asparagine, lysine, alanine, glycine, tyrosine, tryptophan, serine and cysteine and their derivatives, or nonproteinogenic amino acids having in each case one or more amino or carboxy functions, such as, for example β-alanine, ω-amino-1-alkanoic acids, for example 6-aminocaproic acid. The units, preferably from 0 to 15% by weight, are added to the starting mixture of the maleic acid derivatives or, for modification of the chain ends, are reacted therewith after synthesis of the polymer has taken place, preferably with the addition of polar solvents, such as, for example, alcohols or dimethylformamide.

The groups (IV) which increase the molecular masses are introduced by adding the polyfunctional amino or hydroxyl compounds to the reaction mixture. The addition can take place before, during or after neutralization of the maleic monoesters using ammonia. In a preferred embodiment, the crosslinking agents are added after the neutralization. Furthermore, the crosslinking agents can also be added at a later point in the reaction after the reaction mixture has been largely distilled to give the viscous polymer product of maleic monoesters and ammonia, optionally with the addition of acidic or Lewis acid catalysts, such as, for example, titanium(IV) alkoxides. In both embodiments, a further treatment is carried out by distillation (of water, the short-chain alcohol $R^4OH$ and optionally other solvents), optionally under reduced pressure, at from 70 to 220° C., preferably at from 110 to 160° C. The ratio of dicarboxylic acid monomers to the amino or hydroxyl groups of the polyfunctional crosslinking agents can be from 99.5:0.5 to 10:90, preferably from 95:5 to 50:50.

In a further embodiment, the polyfunctional amino or hydroxyl compounds are reacted in a first stage with from 0.1 to 2.0 equivalents, preferably from 0.5 to 1.2 equivalents, of maleic anhydride per hydroxyl or a mino function. The resulting maleic acid derivatives are added to the starting material mixture comprising the maleic monoesters (V) and (VI) before or during neutralization with ammonia.

The procedures described for the addition of the molecular-mass-increasing components can be combined as desired.

The resulting polymers can be post-treated, for example by treatment with ammonia, transesterification catalysts such as, for example, Lewis acid titanium(IV) compounds, with activated carbon or other adsorbents, bleaching with oxidizing agents such as $H_2O_2$, $Cl_2$, $O_3$, sodium chlorite, sodium hypochlorite etc. or reducing agents such as, for example, $NaBH_4$ or $H_2$ in the presence of catalysts, under customary conditions.

Compared with the copolymeric polyaspartic acid derivatives which are prepared without the addition of molecular-mass-increasing groups, the novel copolymers exhibit a significant increase in the resulting molecular masses. They have excellent properties as sequestering agents, as additives for colorants and coatings, as foam stabilizers, surfactants and emulsifiers. In particular, the thermal and long-term stability of O/W and W/O emulsions is beneficially influenced.

The novel polymers can be used as emulsifiers for cosmetic emulsions, for example for lotions having a comparatively low viscosity or creams and ointments having a high viscosity, for applications as skin care compositions, such as, for example, day creams, night creams, care creams, nourishing creams, body lotions, ointments and the like. Other auxiliaries and additives which may be present are customary coemulsifiers, bodying agents, oily substances, superfatting agents, fats, waxes, stabilizers, active ingredients, glycerol, dyes and fragrances.

Suitable bodying agents which may be used are hydrophilic waxes, for example $C_{12}$–$C_{30}$ fatty alcohols, $C_{16}$–$C_{22}$ fatty acids, glycerol mono- and diesters and sorbitan mono- and diesters of saturated fatty acids having from 12 to 22 carbon atoms.

Examples of other suitable coemulsifiers are: addition products of from 2 to 30 mol of ethylene oxide and/or from 0 to 5 mol of propylene oxide with $C_{12}$–$C_{30}$ fatty alcohols and wool wax alcohols, preferably linear, saturated $C_{16}$–$C_{22}$ fatty alcohols; ethylene oxide addition products of glycerol mono- and diesters and sorbitan mono- and diesters of saturated and unsaturated fatty acids having from 6 to 22 carbon atoms; addition products of from 2 to 30 mol of ethylene oxide and/or from 0 to 5 mol of propylene oxide with fatty acids having from 12 to 22 carbon atoms and with alkylphenols having from 8 to 15 carbon atoms in the alkyl group; $C_{12}$–$C_{18}$-fatty acid mono- and diesters of addition products of from 1 to 30 mol of ethylene oxide with glycerol; addition products of ethylene oxide with fats and oils; polyol esters of saturated or unsaturated $C_{12}$–$C_{22}$ fatty acids, including branched or hydroxy-substituted ones, for example esters of pentaerythritol, polyglycerol, sugar alcohols such as sorbitol and polysaccharides, such as cellulose; polysiloxane-polyalkyl-polyether copolymers and their derivatives and hydrophobically modified polyaspartic acid derivatives. The coemulsifiers may also be anionic, cationic, amphoteric and/or zwitterionic surfactants and nonionic surfactants, for example from the groups referred to as compatibility-promoting agents.

It is possible in each case to use any mixtures of the above bodying agents and coemulsifiers.

Examples of suitable oily substances are esters of linear $C_6$–$C_{20}$ fatty acids with linear $C_6$–$C_{20}$ fatty alcohols, esters of branched $C_6$–$C_{13}$ carboxylic acids with linear $C_6$–$C_{20}$ fatty alcohols, esters of linear $C_6$–$C_{20}$ fatty acids with isopropanol or branched alcohols, esters of linear and/or branched $C_6$–$C_{20}$ carboxylic acids with polyhydric alcohols and/or Guerbet alcohols, triglycerides based on $C_6$–$C_{10}$ fatty acids, vegetable and animal oils and fats, branched primary alcohols, substituted cyclohexanes, Guerbet carbonates, dialkyl ethers and/or aliphatic or naphthenic hydrocarbons.

Suitable superfatting agents are, for example, lanolin and lecithin derivatives and their ethoxylates, polyol fatty acid esters, monoglycerides and fatty acid alkanolamides.

Silicone compounds such as polydimethylsiloxanes, cyclodimethicones and amino-, fatty-acid-, alcohol-, epoxy-, fluorine-, and/or alkyl-modified silicone compounds, and waxes such as, for example, beeswax, paraffin waxes or microcrystalline waxes may be present. The emulsions can comprise thickeners, such as polyacrylic acid derivatives or polysaccharides, such as, for example, xanthan, carboxymethylcellulose, hydroxyethylcellulose, cationic cellulose or starch derivatives, cationic chitin or chitosan derivatives, cationic silicone polymers, copolymers of diallylammonium salts, for example with acrylamides, polyethyleneimine. Furthermore, inorganic electrolytes such as alkali metal and alkaline earth metal or ammonium halides, sulfates, nitrates or carbonates, or metal salts of fatty acids, for example magnesium, aluminum or zinc stearate as stabilizers, or zinc salts of ricinoleic acid may be present as deodorizers. Customary sunscreen active ingredients, buffer substances, antioxidants, fragrances, dyes, biogenic active ingredients such as plant extracts or vitamin complexes, pharmaceutical active ingredients and customary moisture-regulating substances such as pyrrolidinedione-2 carboxylate and polyhydroxy compounds such as glycerol, polyglycerols, propanediol, polyethylene glycols, mono- and polysaccharides, may be present.

The emulsions may further comprise lusterizing agents, such as ethylene glycol distearate, solid inorganic additives such as metal oxides, silicates, clay minerals etc. and customary preservatives.

The emulsification can be carried out in a manner known per se, i.e. for example by hot, cold, hot-hot/cold or PIT emulsification.

Depending on the type of polyaspartic acid derivatives and coemulsifiers used, emulsions of the O/W or of the W/O type are obtainable.

In a preferred embodiment of the invention, the emulsions comprise, based on the amount of emulsifier, from to 1 to 99% by weight, preferably from 5 to 50% by weight, of polyaspartic acid derivatives, from 0 to 99% by weight, in O/W emulsions, preferably from 15 to 80% by weight of one or more bodying agents, and from 0 to 99% by weight, preferably from 20 to 75% by weight of further coemulsifiers. The nonaqueous fraction of the emulsions, which is largely composed of the emulsifier/bodying agent and the oily substance content, is usually from 5 to 95% by weight and preferably from 15 to 75% by weight. This means, in the reverse situation, that the emulsions can comprise from 5 to 95% by weight and preferably from 25 to 85% by weight of water, depending on whether the intention is to prepare lotions with a comparatively low viscosity or creams and ointments with a high viscosity.

The novel polyaspartic acid derivatives having a polyamino acid backbone which is similar to naturally occurring structures are mild surfactants, which can be used alone or in combination with anionic, cationic, nonionic, zwitterionic and/or amphoteric surfactants. Solid, liquid or paste preparations are possible, e.g. soap bars, washing lotions, shower gels, shampoos.

The surfactants which can be used in combination with the novel polyaspartic acid derivatives in emulsions or surface-active preparations can, for example, be anionic surfactants from the group of sulfates, sulfonates, carboxylates and mixtures thereof. The anionic groups can be in neutralized form, containing cationic counterions from the group of alkali metals, alkaline earth metals, ammonium or substituted ammonium. Use is made, for example, of alkylbenzenesulfonates, α-olefinsulfonates, α-sulfonated fatty acid esters, fatty acid glycerol ester sulfates, paraffinsulfonates, alkyl sulfates, alkyl polyether sulfates, alkyl sulfosuccinate, fatty acid salts (soaps), fatty acid esters of polylactic acid, N-acylamino acid esters, N-acyltaurates, acylisethionates, ether carboxylates, monoalkyl phosphates, N-acylamino acid derivatives, such as N-acyl aspartates or N-acylglutamates, N-acyl sarcosinates, polyaspartic acid derivatives and others.

The surfactants which can be used in combination with the novel polyaspartic acid derivatives can, for example, be amphoteric or zwitterionic surfactants, for example alkylbetaines, alkylamidoalkylbetaines of the cocoamidopropylbetaine type, sulfobetaines, phosphobetaines, sultaines and amidosultaines, imidazolinium derivatives, amphoglycinates and others.

The surfactants which can be used in combination with the novel polyaspartic acid derivatives can also be, for example, nonionic surfactants, for example oxethylated fatty alcohols, oxethylated alkylphenols, oxethylated fatty acid esters, oxethylated mono-, di- or triglycerides or polyalkylene glycol fatty acid esters. Other nonionic surfactants can originate from the group of alkyl polysaccharides, for example alkyl or alkenyl polyglucosides and their ethoxylation products, sugar esters, for example fatty acid esters of glucose, saccharose, fructose or of methyl glucoside, sorbitol fatty acid esters and sorbitan fatty acid esters (optionally oxethylated), polyglycerol esters, fatty acid alkanolamides, N-acylamino sugar derivatives, for example N-acylglucamines, long-chain tertiary amine oxides or phosphine oxides and dialkyl sulfoxides.

The cationic surfactants which are used in combination with the novel polyaspartic acid derivatives can, for example, be chosen from the group of quaternary ammonium compounds, quaternized protein hydrolyzates, alkylamido amines, quaternary ester compounds, quaternary silicone oils or quaternary sugar and polysaccharide derivatives.

The surfactants which are used in combination with the novel polyaspartic acid derivatives can also be any combination of two or more surfactants from the abovementioned categories.

The surfactant preparations according to the invention can comprise further auxiliaries and additives, such as, for example, water and solvents, for example from the group of alcohols and polyols, thickeners, opacifiers, e.g. glycol ester derivatives; moisturizers, emollients such as animal and vegetable oils, carboxylic esters, lanolin, beeswax, silicones; polymeric agents for improving the feel on the skin, conditioning, care or pharmaceutically active constituents such as, for example, cationic or amphoteric polymers, proteins and protein derivatives, lanolin derivatives, pantothenic acid, betaine, polydimethylsiloxanes or their derivatives, sunscreen active ingredients and solubilizers, stabilizers, buffer substances, fragrances, preservatives and/or dyes.

The surfactant preparations comprising polyaspartic acid derivatives can advantageously be used in, for example, hair shampoo, shower preparation, bubble bath preparation, hand, face and intimate area cleansing lotion, liquid soap, soap bar, shaving cream, handwashing paste, dishwashing detergents which are gentle on the skin, cleaner for smooth surfaces and in toothpaste.

The novel polyaspartic acid derivatives can advantageously be used as dispersants, for the preparation of aqueous pigment pastes. To this end, the hydrophobically modified polyaspartic acid derivatives are neutralized advantageously using prior art neutralizing agents, in particular amines. Particular preference is here given to using dimethylethanolamine or 2-amino-2-methylpropanol. For the preparation of aqueous pigment pastes, from 0.1 to 100% by weight, preferably from 0.5 to 50% by weight, in particular from 2 to 15% by weight, based on the weight of the pigments, are used. The hydrophobically modified polyaspartic acid derivatives can, for the novel use, either be mixed beforehand with the pigments to be dispersed, or be dissolved directly in the dispersing medium (water, possible additions of glycol) prior to or at the same time as the addition of the pigments and any other solids. Neutralization can take place before or during the preparation of the pigment pastes. Preference is given to using polyaspartic acid preparations which have already been partially or completely neutralized.

The novel polyaspartic acid derivatives can also be used in any mixtures with other, prior art dispersion additives, for example from the group of fatty acid alkoxylates, poly (meth)acrylates, polyesters, polyethers etc.

In this connection, examples of pigments which may be mentioned are inorganic or organic pigments, and carbon blacks. Examples of inorganic pigments are titanium dioxide and iron oxides. Suitable organic pigments are, for example, azo pigments, metal complex pigments, phthalocyanine pigments, anthraquinoid pigments, polycyclic pigments, in particular those from the thioindigo, quinacridone, dioxazine, pyrrolopyrrole, naphthalenetetracarboxylic acid, perylene, isoamidolin(on)e, flavanthrone, pyranthrone or isoviolanthrone series. The novel polyaspartic acid derivatives can be used as dispersants, for example for coatings and colorants.

Fillers which can, for example, be dispersed in aqueous coatings are, for example, those based on kaolin, talc, other silicates, chalk, glass fibers, glass pearls or metal powders.

Suitable coating systems into which the novel pigment pastes can be incorporated are any aqueous 1-component or 2-component coatings. Examples include aqueous 1-component coatings, such as, for example, those based on alkyd, acrylate, epoxy, polyvinyl acetate, polyester or polyurethane resins, or aqueous 2-component coatings, for example those based on hydroxyl-group-containing polyacrylate or polyester resins with melamine resins or optionally blocked polyisocyanate resins as crosslinkers. Polyepoxy resin systems may likewise also be mentioned.

EXAMPLES

Comparative Examples 1 and 2

Poly(aspartic acid-co-alkyl aspartate)

The polyaspartic esters were prepared as described in accordance with DE 195 45 678 A by reacting the starting materials (monoethyl maleate, monoalkyl maleate, dissolved in methylisobutyl ketone) with from 1.0 to 1.5 equivalents of ammonia gas and distillation of the reaction mixture under reduced pressure at from 110 to 140° C. for from 4 to 6 h.

The degrees of esterification were determined using NMR spectroscopy, the average molecular masses were determined by gel permeation chromatography (column 2×SDV100 Å/microgel 100 Å; tetrahydrofuran/oxalic acid, calibrated against PMMA)

| EXAMPLE | ALKYL RADICAL | STARTING MATERIAL: MOL OF ALKYL MALEATE | STARTING MATERIAL: MOL OF ETHYL MALEATE | PRODUCT: MOL % OF ALKYL ESTER | PRODUCT: MOL % OF ETHYL ESTER | MOL % OF ACID | $M_W$ (GPC) |
|---|---|---|---|---|---|---|---|
| 1 | decyl | 1.0 | 3.0 | 20 | 3 | 77 | 1200 |
| 2 | cetyl | 1.2 | 2.8 | 27 | 6 | 67 | 1800 |

Example 3

300 g of the product from Example 1 were mixed with 70 g of 1,6-diaminohexane at 135° C., and the mixture was stirred at 140° C. for 8 h under distillation conditions. GPC:$M_w$=2500

Example 4

400 g of the product from Example 1 were mixed with 86 g of 1,6-hexanediol at 120° C., 4 g of tetrabutyl titanate are added and the mixture is distilled at 145° C. and 200 mbar for 8 h. GPC:$M_w$=3900

Example 5

Following the procedure of Example 3, 400 g of the product from Ex. 2 were reacted with 140 g of 1,6-diaminohexane. GPC:$M_w$=9800

Example 6

340 g (1 mol) of cetyl maleate, 286 g (2 mol) of ethyl maleate and 79 g (0.25 mol) of the reaction product of maleic anhydride and 1,6-hexanediol (1:1) were dissolved in 4-methyl-2-pentanone and treated with 4 mol of ammonia gas. Distillation was carried out at from 110 to 130° C. under reduced pressure for 5 h. GPC:$M_w$=6200

Examples 7 to 10

O/W Emulsions containing polyaspartic acid derivatives

| | |
|---|---|
| Cetylpolyaspartate from Example 2, 4, 5 or 6 (25% in water, pH 5.5) | 2.0% |
| Glycerol | 3.0% |
| Preservative | 0.1% |
| Water | 70.4% |
| Glycerol monostearate (Tegin ® M, Th. Goldschmidt AG) | 4.5% |
| Caprylic/capric triglyceride, (Tegosoft ® CT, Th. Goldschmidt AG) | 20.0% |

The aqueous phase and the oily substance/glycerol monostearate mixture were mixed at 70° C., and vigorously processed using a rotor-stator homogenizer (SG/220V, 2 min). The water separation of the O/W emulsions was determined after storage for 2 d at 20° C. and after storage for a further 7 d at 45° C. The sensory evaluation of the samples showed, in the case of Ex. 5, no change in the creamy consistency during storage, and in the case of the comparison, a noticeable deterioration.

| EXAMPLE | EMULSIFIER FROM EXAMPLE | WATER SEPARATION AFTER 2 DAYS/20° C. (% BY VOLUME) | WATER SEPARATION AFTER 28 DAYS/45° C. (% BY VOLUME) |
|---|---|---|---|
| 7 | 2 | <0.1% | 6 |
| 8 | 4 | <0.1% | 1 |
| 9 | 5 | <0.1% | 0.5 |
| 10 | 6 | <0.1% | 2 |

These results show the improvement in the emulsion stability of the polyaspartic esters modified using polyfunctional agents.

Example 11

Surfactant preparations containing polyaspartic acid derivatives

| FORMULATION | A (% BY WEIGHT) | B (% BY WEIGHT) |
|---|---|---|
| Poly (aspartic acid-co-decyl asparate) as in Example 3, (50% strength in water, pH 5,5) | 0.0% | 1.0% |
| Texapon ® N28 (28% sodium lauryl ether sulfate (Henkel KGaA)) | 21.4% | 21.4% |
| Tego ® betaine F50 (37.5% cocamidopropylbetaine, Th. Goldschmidt AG) | 16.0 | 16.0 |
| Water ad 100%, pH ad 6.0 | | |

The foaming properties of the surfactant mixture are determined by frothing up a dilute surfactant solution. (0.5% by weight of active detergent substance, 8° German hardness, 30° C., Ystral guidebeam mixer, 750 W, 2 min)

| MIXTURE | FOAM VOLUME [ml] | WATER SEPARATION 10 MIN [ml] | FOAM DENSITY [g/ml] |
|---|---|---|---|
| A | 1490 ± 17 | 240 ± 2.0 | 0.208 ± 0.002 |
| B | 1584 ± 11 | 231 ± 2.9 | 0.193 ± 0.003 |

This example demonstrates the positive effect of the polyaspartic acid derivatives on the foaming behavior of surfactant systems.

Example 12

| Formulation for a shower gel concentrate | |
|---|---|
| Poly(aspartic acid-co-decyl aspartate), as in Example 3, (48% strength in water, pH 5,5) | 9.0% |
| Texapon ® N70 (70% sodium lauryl ether sulfate, Henkel KGaA) | 32.0% |
| Tagat ®R40 (PEG-40 ethoxylate of hydrogenated castor oil, Th. Goldschmidt AG) | 5.0% |
| Tego ® glucoside 810 (60% caprylic/capric glucoside, Th. Goldschmidt AG) | 9.0% |
| Citric acid (20%) | 0.9% |
| NaCl (25%) | 8.5% |
| Water | 17.6% |
| Tego ® betaine F50 (37.5% cocoamidopropyl-betaine, Th. Goldschmidt AG) | 18.0% |

Example 13

| O/W-based care cream | |
|---|---|
| Poly(aspartic acid-co-cetyl aspartate), as in Example 5, (50% strength in water, pH 5,5) | 4.5% |
| Tego ® care 450 (polyglyceryl-3 methylglucoside distearate, Th. Goldschmidt AG) | 1.0% |
| Tegin ® M (glyceryl stearate, Th. Goldschmidt AG) | 0.5% |
| Tego ® alkanol 18 (stearyl alcohol, Th. Goldschmidt AG) | 0.3% |
| Avocado oil | 12.0% |
| Tegosoft ® CT (caprylic/capric triglyceride, Th. Goldschmidt AG) | 9.0% |
| Glycerol | 3.0% |
| Water | 69.7% |
| NaOH (10%) ad pH 5.5 | |

While the invention has been particularly shown and described with respect to preferred embodiments thereof, it will be understood by those skilled in the art that the foregoing and other changes in form and details may be made therein without departing from the spirit and scope of the invention.

What is claimed is:

1. A copolymer derived from polyamino acids, in which at least 75 mol % of the units present consist of structural units of the general formulae (I), (II) and (III)

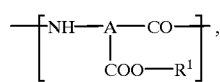 (I)

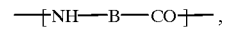 (II)

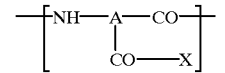 (III)

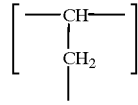 (A1)

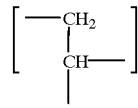 (A2)

in which the structural elements A are identical or different trifunctional hydrocarbon radicals having 2 carbon atoms of the type (A1) or (A2), where one copolymer consists of at least three units of the formula (I), where $R^1$ comprises $R^2$, $R^3$ or $R^4$, where $R^2$ is at least one radical from the group of alkali metals, alkaline earth metals, hydrogen or ammonium, $(NR^5R^6R^7R^8)^+$; where $R^5$ to $R^8$ independently of one another are hydrogen, alkyl or alkylene having from 1 to 22 carbon atoms or hydroxyalkyl having from 1 to 22 carbon atoms and from 1 to 6 hydroxyl groups and/or their acylation products containing $C_1$- to $C_{22}$-carboxylic radicals; $R^3$ is identical or different, straight-chain or branched, saturated or unsaturated alkyl or alkenyl radicals $R^9$ having from 6 to 30 carbon atoms, or radicals of the structure $—Y—R^9$, where Y is an oligo- or polyoxyalkylene chain having from 1 to 100 oxyalkylene units; $R^4$ is identical or different, straight-chain or branched, saturated or unsaturated alkyl or alkenyl radicals having from 1 to 5 carbon atoms; the units of the formula (II) are proteinogenic or nonproteinogenic amino acids and are present in an amount of not more than 20% by weight, and X in formula (III) is at least one di- or polyfunctional radical derived from molecular-mass-increasing agents; and at least in each case one radical $R^1$ is $R^2$, at least one radical $R^1$ is $R^3$, and at least one radical $R^1$ is X, said copolymer having a molecular weight, $M_w$, of about 2500 or above.

2. The copolymer as claimed in claim 1, in which at least one radical $R^1$ has the meaning of $R^4$.

3. The copolymer as claimed in claim 1, in which $R^3$ are identical or different, straight-chain or branched, saturated or unsaturated alkyl or alkenyl radicals having from 8 to 24 carbon atoms.

4. The copolymer as claimed in claim 1, comprising, as molecular-mass-increasing agents, di- or polyhydroxy compounds, di- or polyamino compounds, or aminoalcohols or mixtures, having a linear, branched or cyclic, saturated, unsaturated or aromatic hydrocarbon structure, optionally oxo- or aza-substituted with O or N atoms in the chain.

5. The copolymer as claimed in claim 1, comprising, as molecular-mass-increasing agents, linear 1, (-alkanediols, glycerol, sorbitol, 1,2-propylene glycol, linear 1,ω-diaminoalkanes, lysine, ethanolamine, diethanolamine, triethanolamine, sugar derivatives, oligo- and polysaccharides, the addition products of ethylene oxide and/or propylene oxide with said compounds, polyvinyl alcohol, oligo- and polyethylene glycols and/or ethylene oxide-propylene oxide copolymers.

6. A process for the preparation of the copolymers as claimed in claim 1, which comprises reacting esters of α,β-unsaturated dicarboxylic acids or their ammonium salts, in particular maleic acid derivatives of the general formulae (V) and (VI)

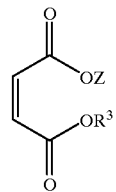

(V)

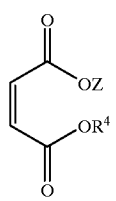

(VI)

alone or in a mixture with one another, with ammonia, and converting them into the polymer and then treating them with molecular-mass-increasing agents, where Z is hydrogen and/or ammonium, and $R^3$ and $R^4$ are the abovementioned radicals, optionally in the presence of up to 20% by weight of proteinogenic or nonproteinogenic amino acids or their derivatives of the general formula (II), and optionally in further stages, by hydrolysis, producing groups of the structure of the formula (I) where $R^1$ has the meaning of $R^2$, having the abovementioned definition of $R^2$.

7. The process as claimed in claim 6, which comprises reacting esters of α,β-unsaturated dicarboxylic acids or their ammonium salts, in particular maleic acid derivatives of the general formulae (V) and (VI), in the presence of molecular-mass-increasing agents with ammonia, and converting into the polymer.

8. A cosmetic emulsion comprising a copolymer as claimed in claim 1, wherein the nonaqueous fraction comprises from 5 to 99% by weight of oily substances from the group consisting of esters of linear $C_6$–$C_{20}$-fatty acids with linear $C_6$–$C_{20}$-fatty alcohols, esters of branched $C_6$–$C_{13}$-carboxylic acids with linear $C_6$–$C_{20}$-fatty alcohols, esters of linear $C_6$–$C_{20}$-fatty acids with branched alcohols, esters of linear and/or branched $C_6$–$C_{20}$-carboxylic acids with polyhydric alcohols and/or Guerbet alcohols, triglycerides based on $C_6$–$C_{10}$-fatty acids, vegetable and animal oils and fats, branched primary alcohols, substituted cyclohexanes, Guerbet carbonates, dialkyl ethers and/or aliphatic or naphthenic hydrocarbons.

9. The cosmetic emulsion as claimed in claim 8, comprising hydrophilic waxes selected from the group consisting of $C_{12}$–$C_{30}$-fatty alcohols, wool wax alcohols, $C_6$–$C_{22}$-fatty acids, glycerol mono- and diesters and sorbitan mono- and diesters of saturated fatty acids having from 12 to 22 carbon atoms.

10. The cosmetic emulsion as claimed in claim 8, comprising one or more coemulsifiers selected from the group consisting of the addition products of ethylene oxide or ethylene oxide and propylene oxide with $C_{12}$–$C_{30}$-fatty alcohols and wool wax alcohols, the ethylene oxide addition products of glycerol mono- and diesters and sorbitan mono- and diesters of saturated and unsaturated fatty acids having from 6 to 22 carbon atoms, of the addition products of ethylene oxide and/or propylene oxide with fatty acids having from 12 to 22 carbon atoms and with alkylphenols having from 8 to 15 carbon atoms in the alkyl group, of $C_{12}$–$C_{18}$-fatty acid mono- and diesters of addition products of ethylene oxide with glycerol, of addition products of ethylene oxide with fats and oils, of polyol esters of saturated or unsaturated $C_{12}$–$_{22}$-fatty acids, including branched or hydroxy-substituted ones, of polysiloxane-polyalkyl-polyether copolymers and their derivatives, of anionic surfactants, cationic surfactants, nonionic surfactants and zwitterionic or amphoteric surfactants.

* * * * *